United States Patent
Tsung et al.

(10) Patent No.: US 6,884,362 B2
(45) Date of Patent: Apr. 26, 2005

(54) MASS PRODUCTION OF CROSS-SECTION TEM SAMPLES BY FOCUSED ION BEAM DEPOSITION AND ANISOTROPIC ETCHING

(75) Inventors: Lancy Tsung, Plano, TX (US); Adolfo Anciso, Garland, TX (US)

(73) Assignee: Texas Instruments Incorporated, Dallas, TX (US)

( * ) Notice: Subject to any disclaimer, the term of this patent is extended or adjusted under 35 U.S.C. 154(b) by 62 days.

(21) Appl. No.: 10/368,321

(22) Filed: Feb. 18, 2003

(65) Prior Publication Data

US 2003/0150836 A1 Aug. 14, 2003

Related U.S. Application Data

(62) Division of application No. 09/921,324, filed on Aug. 2, 2001, now Pat. No. 6,786,978.
(60) Provisional application No. 60/222,462, filed on Aug. 3, 2000.

(51) Int. Cl.⁷ .................................................. H01L 21/00
(52) U.S. Cl. ............................... 216/2; 216/48; 216/52; 216/60; 216/79
(58) Field of Search ................................. 216/2, 48, 50, 216/51, 52, 60, 61, 67, 75, 79

(56) References Cited

U.S. PATENT DOCUMENTS

| | | | | |
|---|---|---|---|---|
| 5,525,806 A | * | 6/1996 | Iwasaki et al. | 250/492.21 |
| 5,798,529 A | * | 8/1998 | Wagner | 250/492.21 |
| 5,940,678 A | * | 8/1999 | Doong et al. | 438/14 |
| 5,990,478 A | * | 11/1999 | Liu | 250/307 |
| 6,177,670 B1 | * | 1/2001 | Sugiyama | 250/307 |
| 6,395,347 B1 | * | 5/2002 | Adachi et al. | 427/526 |
| 6,420,703 B1 | * | 7/2002 | Wu et al. | 250/311 |

FOREIGN PATENT DOCUMENTS

| | | | | | |
|---|---|---|---|---|---|
| JP | 06061320 A | * | 3/1994 | | H01L/21/66 |
| JP | 07151658 A | * | 6/1995 | | G01N/1/32 |

* cited by examiner

*Primary Examiner*—Allan Olsen
(74) *Attorney, Agent, or Firm*—Yingsheng Tung; Wade James Brady, III; Frederick J. Telecky, Jr.

(57) ABSTRACT

A method of preparing a TEM sample. A focused ion beam is used to deposit a mask on the material to be sampled. Reactive ion etching removes material not protected by the mask, leaving a wall thin enough to be imaged by TEM.

14 Claims, 3 Drawing Sheets

MASS PRODUCTION OF CROSS-SECTION TEM SAMPLES BY FOCUSED ION BEAM DEPOSITION AND ANISOTROPIC ETCHING

This is a divisional application of Ser. No. 09/921,324 filed Aug. 2, 2001, now U.S. Pat. No. 6,786,978, which claims priority under 35 USC 119(e)(1) of provisional application Ser. No. 60/222,462, filed Aug. 3, 2000.

BACKGROUND AND SUMMARY OF THE INVENTION

This application relates generally to semiconductor device fabrication, and specifically to preparation of TEM samples for testing internal structure and chemistry of fabricated devices.

BACKGROUND

Transmission electron microscopes (TEMs) were developed because of the resolution limitations of light microscopes, which are imposed by the wavelength of visible light. TEMs are among the most useful and versatile tools for characterization of materials. In contrast to scanning electron microscopes, which only image the surface of a material, TEM allows analysis of the internal structure of a sample.

As critical dimensions of integrated circuits have become smaller and more complex, TEM analysis has been relied on as an essential technique for high spatial resolution imaging at the atomic level. TEM samples must be transparent to the electron beam in order to image the internal structure of the sample. In terms of a TEM, "thin" means the specimen must transmit sufficient electrons such that enough intensity falls on the screen or photographic plate to create an interpretable image in a reasonable time. This is a function of the electron energy and the size and weight of the atoms comprising the specimen. Though higher beam energy allows thicker samples to be imaged, the danger of damage to the sample from the electron beam increases. High sample yield and fast turn-around time are also important economically.

Samples are typically thinned by cutting out or grinding down a tiny piece of the specimen which is further thinned by an ion milling process or use of a focused ion beam. The mechanical thinning (i.e., the cutting or grinding) is required because ion beams typically remove strips of material with thicknesses in the tens or hundreds of nanometers, and large scale thinning using such precise devices is time consuming and therefore expensive. Samples prepared this way can reach thicknesses of only a few hundred angstroms Focused ion beams (FIBs) used in ion milling (which bombards a material with ions to remove parts of the targeted material) accelerate ions using electric fields. A variety of ion species may be used, including Ga, Si, Au, Co, and Pr. Focused ion beam methods can be used for implantation, sputtering, deposition, micro-machining, and ion beam lithography, depending on the setup and the energies used. High resolution of FIBs allows identification of precise areas to be sampled, which is very important in TEM since only a tiny relative area may be viewed due to the magnification levels used. Using FIBs to thin samples also gives operators better control than mechanical polishing techniques, resulting in higher yield. Most FIB techniques provide reliable and repeatable results for routine analysis.

An example of using FIB to prepare samples is found in a paper by Morris et al., "A Technique For Preparing TEM Cross-Sections to a Specific Area Using the FIB," Proceedings of ISTFA 1991, pp. 417–427, which is hereby incorporated by reference. First the sample is mechanically thinned to make the FIB use practical. The FIB removes the remainder of unwanted material, leaving an electron transparent wall. The process uses optical means to choose an area for sampling, and mechanical lapping reduces the area to a thickness of about 30 micrometers. Either one-sided or two-sided ion milling is used to further thin the material down to thicknesses of less than several hundred nanometers.

Use of FIB methods in sample preparation has reduced the time required to prepare samples for TEM analysis down to only a few hours. However, for today's stringent device requirements, one sample alone is often not enough to sufficiently characterize and qualify a specific process. When multiple samples are taken, a few hours sample preparation time can turn into days or even weeks.

A different method of TEM sample preparation has been reported using electron beam lithography and reactive ion etching (RIE) to etch out a sufficiently thin sample. An example process can be found in a paper by Wetzel, et al., "On the Preparation of Cross-Sectional TEM Samples using Lithographic Processing and Reactive Ion-Etching," Ultramicroscopy v.29, pp. 110–114 (1989), which is hereby incorporated by reference. A photoreactive compound is spun on the substrate and cured, followed by exposure with an electron beam lithographic device. After development, the process leaves a stencil of the e-beam exposure. This mask has a selectivity difference with the underlying material to be sampled, so that during RIE the mask is nearly consumed but the sample is etched to define a thin electron transparent wall. The selectivity of the mask material used determines the height of the sample wall. This process, though reported years ago, has not been adopted for widescale use because of high cost in tools and masks required.

There is therefore a need in the art for a process of preparing TEM samples that requires less preparation time to make TEM sampling a viable part of semiconductor analysis and manufacturing.

Mass Production Cross-Section TEM Samples by Focused Ion Beam Deposition and Anisotropic Etching The present application discloses a method of producing cross-section TEM samples using a focused ion beam to deposit a mask and an anisotropic etch process to etch around the mask. The preferred embodiment uses focused ion beam deposition and reactive ion etching, as follows. The region of interest is imaged using a scanning electron microscope. The FIB is used at a low power to deposit a thin strip of platinum (though other mask materials can be used) which acts as a mask when surrounding material is removed by etching. During etching, material on both sides of the platinum strip are removed in a single etch process, leaving a thin wall that is transparent to electron transmission sufficient for imaging through a TEM. After RIE, the sample is ready for TEM.

Though the preferred embodiment uses reactive ion etching, any low discharge etching process that has the required anisotropy can be used.

Advantages of the disclosed methods and structures, in various embodiments, can include one or more of the following:

saves preparation time of multiple TEM samples;

samples used for measuring critical dimension can be obtained from many sites within a die as well as from different dies of a wafer.

BRIEF DESCRIPTION OF THE DRAWINGS

The disclosed inventions will be described with reference to the accompanying drawings, which show important sample embodiments of the invention and which are incorporated in the specification hereof by reference, wherein:

FIG. 2a shows a sample with a mask-defining box drawn in.

DETAILED DESCRIPTION OF THE PREFERRED EMBODIMENTS

The numerous innovative teachings of the present application will be described with particular reference to the presently preferred embodiment. However, it should be understood that this class of embodiments provides only a few examples of the many advantageous uses of the innovative teachings herein. In general, statements made in the specification of the present application do not necessarily delimit any of the various claimed inventions. Moreover, some statements may apply to some inventive features but not to others.

Figure 1:
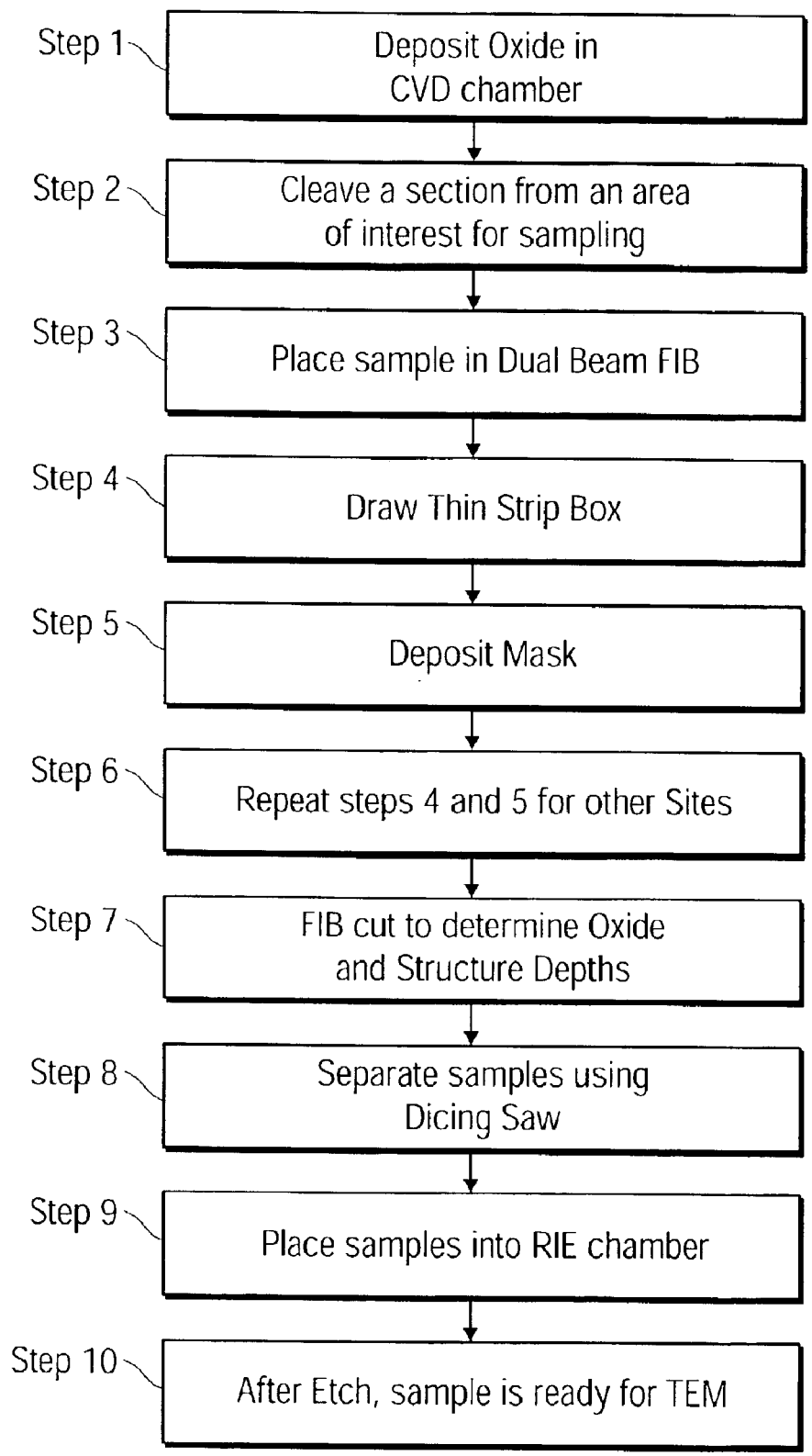
FIG. 1 shows a process flow for the preferred embodiment.

The preferred embodiment is described with reference to the numbered figures. FIG. 1 shows a process flow for the preferred embodiment.

The basic requirement of a TEM sample dictates that the sample must be thin enough to be penetrated by the electron beam and thin enough to avoid multiple scattering, which causes image blurring. The disclosed innovative technique deposits a platinum mask on the area to be sampled and uses the RIE to remove material around the masked area in quantity all at once instead of layer by layer milling with current FIB techniques.

Figure 2A:
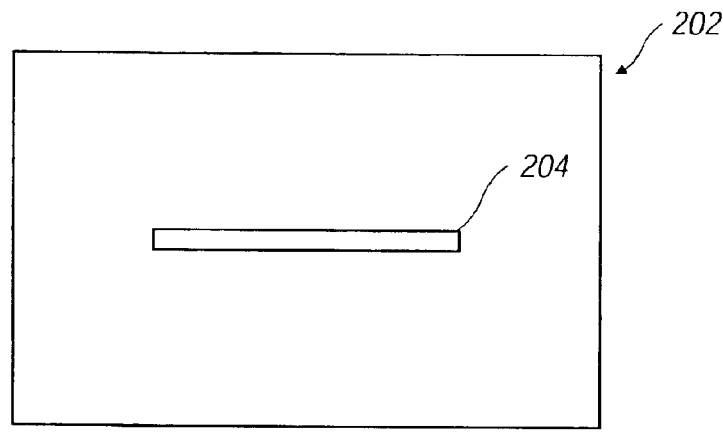

The FIB used in the preferred embodiment uses Ga ions. To avoid Ga beam damage during FIB platinum deposition, a thin oxide layer is deposited in a plasma enhanced CVD chamber (Step 1). In the preferred embodiment, silicon oxide is deposited to a thickness of approximately 180 nm at the center of the wafer. Depositing the oxide on the entire wafer takes approximately 5 minutes. The wafer is then cleaved to separate a piece from an area of interest for sampling (Step 2). The sample to be analyzed is then placed in a dual beam FIB machine capable of generating SEM surface imaging and FIB deposition (Step 3). The region to be sampled is imaged in SEM mode at adequate magnification. Once the proper area is located, a thin strip box about 0.13 micrometers wide, 0.6 micrometers tall and 18 micrometers long is drawn over the interested area (Step 4). FIG. 2a shows the sample after Step 4. The sample 202 has drawn on it a thin box 204 that will define the mask.

Figure 2B:
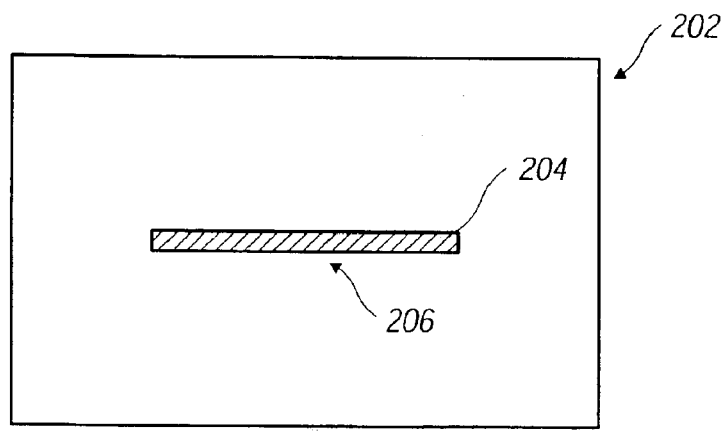
FIG. 2b shows a sample with a mask deposited.
Figure 3:
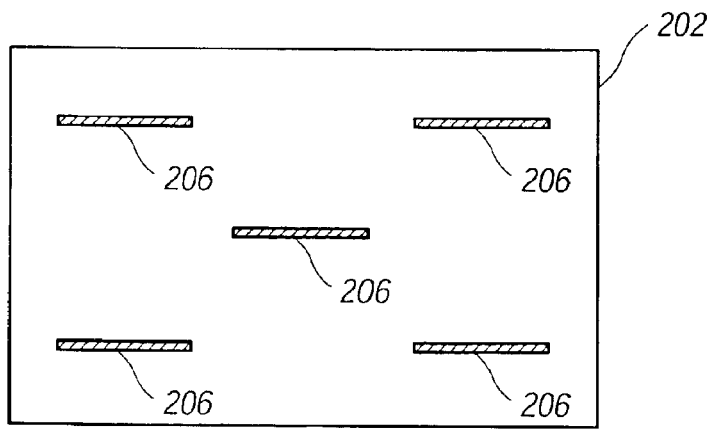
FIG. 3 shows multiple masks placed on a sample for measuring characteristics at different locations.

The platinum needle that dispenses an organic Pt gas is inserted into the chamber next, positioned to direct the gas directly on the surface within the platinum slot. Then the area is imaged in ion beam mode using a single frame update. Once the alignment is set, the needle valve can be opened to release the gas, and the ion beam is turned on to start deposition of the Pt mask (Step 5). FIG. 2b shows the sample after Step 5. The box 204 on the sample 202 is now filled in with platinum to form the mask 206. The deposition occurs through ion beam-induced decomposition of the organic Pt gas at the surface of the sample. The ion beam current should therefore be set at a low value to enhance pattern definition. A current of 11 pA is used to deposit a 0.6 micrometer thick mask in the preferred embodiment. Once deposition is complete, the sample can be moved to a different area or structure for depositing additional mask strips (Step 6). Several platinum masks can be deposited in this way to obtain several samples of different locations on the circuit. FIG. 3 shows a sample 202 with multiple masks 206 deposited on its surface.

The oxide and structure thickness must be known to set etch time. Therefore the thickness is measured at a location relatively far away from the area of interest by making an FIB cut (Step 7).

The samples are then cut out using a dicing saw with the FIB marked area in the center of the cut-out area (Step 8). Typical dicing cut samples have a top-hat cross section, with a top width of about 30 micrometers, and a bottom width of about 180 micrometers. The length of the sample is 2.95 mm as required by the dimension of the TEM double tilt holder. The cut pieces are removed and inserted in a plate holder with the top surface standing up. The sample holder and sample are then put into the RIE chamber (Step 9). A mixture of $CF_4$, $O_2$, and $CHF_3$ gases (40:3:5 volume ratio) are used to give optimum etch rate, minimum polymer residue, and to maintain anisotropic etch properties.

At RF power set at 500 watts and gas pressure at 30 mTorr, the etch rate is roughly 100 nm/minute. A slight amount of overetch into the silicon substrate is required to provide a thin area in silicon for tilting the zone axis during TEM imaging. After the RIE process, the sample is ready for TEM imaging (Step 10).

Figure 4A:
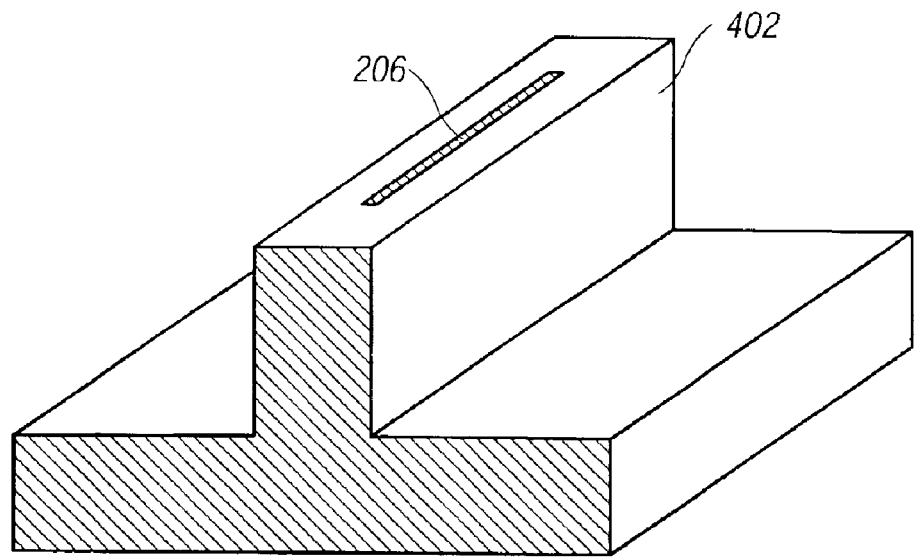
FIG. 4a shows a die-cut sample before etching.
Figure 4B:
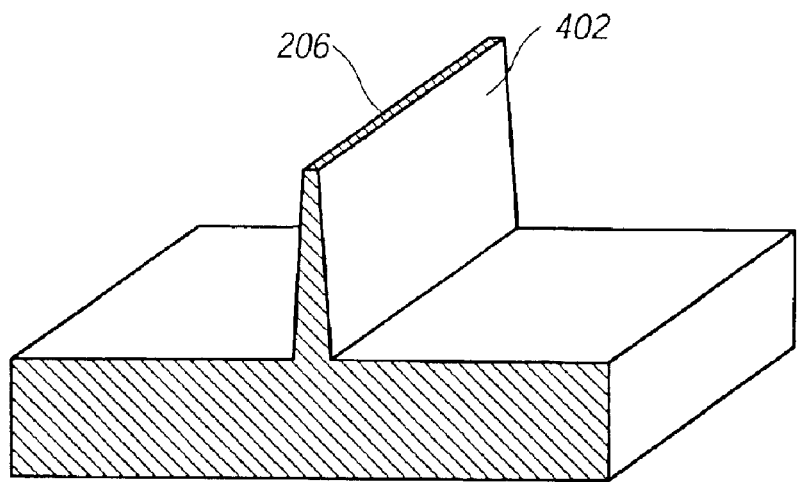
FIG. 4b shows a sample after etching.

FIG. 4a shows a sample ready for etching. The etching plasma has different selectivity for the underlying material 402 than the mask 206, causing the etch process to remove large quantities of material 402 while leaving the mask 206 relatively intact (although some erosion of the mask does occur). FIG. 4b shows the sample after etching. The underlying material 402 is now reduced to a thin wall that is sufficiently thin for imaging in a TEM.

The greatest benefit of this technique is the time it saves in preparing multiple TEM samples. The preparation time for the disclosed innovative technique is 50 minutes for one sample and about 6 hours for 10 samples. Previous FIB milling techniques require about 4 hours to prepare one sample and 40 hours for 10 samples.

Another benefit arises for wafers pulled immediately after etch for poly gate profile and critical dimension (cd) measurement. Poly cd measurement is a critical issue for devices with aggressive design rules. Traditional in-line SEM metrology and electrical measurement can no longer give accurate data on transistors with less than 0.2 micrometer lines, and TEM appears to be the only tool for measuring gate cd. Because the innovative method of the present application easily allows multiple samples to be taken in a reduced time compared to previous methods, samples measuring cd can be obtained from many sites within a die as well as from different dies of a wafer to control the cd variation due to structure density and center/edge issues.

Definitions:

Following are short definitions of the usual meanings of some of the technical terms which are used in the present application. (However, those of ordinary skill will recognize whether the context requires a different meaning.) Additional definitions can be found in the standard technical dictionaries and journals.

FIB: Focused Ion Beam. Accelerating ions usually by using electric fields to various energies, used for implantation, sputtering, deposition, micro-machining, and ion beam lithography.

SEM: Scanning Electron Microscope. A device that uses a beam of electrons to image the surface of a target material.

TEM: Transmission Electron Microscope. A device that uses a beam of electrons to image a sample by passing electrons through the sample and observing the resulting pattern.

Thin: In the context of TEM, "thin" means transparent enough to electron microscopy so that useful images may be produced.

Modifications and Variations

As will be recognized by those skilled in the art, the innovative concepts described in the present application can be modified and varied over a tremendous range of applications, and accordingly the scope of patented subject matter is not limited by any of the specific exemplary teachings given, but is only defined by the-issued claims.

In one class of embodiments, other materials are substituted for the mask material. For instance, a tungsten mask may be deposited instead of platinum. Any metal with the necessary etch selectivity could serve as a mask material. The mask material may also be deposited by other particle beams, such as neutral atoms, and is within the contemplation of the present application so long as the innovative features disclosed herein are observed.

In another class of embodiments, the etching is done using a different recipe, using different chemicals or the same chemicals in different ratios. Such variations are within the contemplation of the present application.

The process flow may also be varied. For instance, Steps 1 and 2 from FIG. 1 may be done in reverse order, cleaving a section from an area of interest before deposition of the oxide. Other changes may also be made, within the confines of process limitations.

The samples prepared by the disclosed innovations may also be suitable for other uses, such as a scanning transmission electron microscope or similar devices.

Additional general background, which help to show the knowledge of those skilled in the art regarding variations and implementations of the disclosed inventions, may be found in the following documents, all of which are hereby incorporated by reference: FOCUSED ION BEAM INDUCED DEPOSITION—A REVIEW, J. Melngailis, SPIE Vol. 1465: Electron Beam, X-Ray, and Ion Beam Submicrometer Lithographies for Manufacturing, 36 (1991); FOCUSED ION BEAM INSULATOR DEPOSITION: AN ADVANCED TECHNIQUE FOR DEVICE MODIFICATION, Abramo et al., Proceedings of the European Symposium on the Reliability of Electron Devices, pp. 313–317 (1995); FOCUSED ION BEAM INDUCED INSULATOR DEPOSITION AT DECREASED BEAM CURRENT DENSITY, Abramo et al., Proceedings of the 35th Annual International reliability Physics Symposium, pp. 66–71, Apr. 8–10, 1997; Coburn, PLASMA ETCHING AND REACTIVE ION ETCHING (1982); HANDBOOK OF PLASMA PROCESSING TECHNOLOGY (ed. Rossnagel); PLASMA ETCHING (ed. Manos and Flamm 1989); PLASMA PROCESSING (ed. Dieleman et al. 1982); Schmitz, CVD OF TUNGSTEN AND TUNGSTEN SILICIDES FOR VLSI/ULSI APPLICATIONS (1992); METALLIZATION AND METAL-SEMICONDUCTOR INTERFACES (ed. Batra 1989); VLSI METALLIZATION: PHYSICS AND TECHNOLOGIES (ed. Shenai 1991); Murarka, METALLIZATION THEORY AND PRACTICE FOR VLSI AND ULSI (1993); HANDBOOK OF MULTI-LEVEL METALLIZATION FOR INTEGRATED CIRCUITS (ed. Wilson et al. 1993); Rao, MULTILEVEL INTERCONNECT TECHNOLOGY (1993); CHEMICAL VAPOR DEPOSITION (ed. M. L. Hitchman 1993); and the semiannual conference proceedings of the Electrochemical Society on plasma processing.

What is claimed is:

1. A method for making an integrated TEM sample holder with a sample, comprising:

a. providing a semiconductor wafer having a top surface with a viewing site and a substantially parallel bottom surface;

b. defining on the top surface of the semiconductor wafer an area of substantially rectangular shape containing the viewing site and dimensioned suitably for engaging a TEM double-tilt holder;

c. depositing a metallic layer in the viewing-site area with a focused ion-beam means;

d. shaping a base of the integrated TEM sample holder for engaging a TEM double-tilt holder including the steps of:

i. mechanically severing from the semiconductor wafer a portion of semiconductor material having a first top surface containing the viewing site and a opposing bottom surface area corresponding to the rectangular-shaped area and four sidewalls substantially perpendicular to the top surface and the bottom surface, and;

ii. mechanically removing a portion of semiconductor material downwardly from the first top surface to create a narrow center portion extending upwardly from the base of the sample holder, the center portion having two substantially parallel sidewalls substantially perpendicular to the bottom surface; and e. thinning a portion of the center-portion material with a reactive ion etching means downwardly from the top surface of the TEM holder adjacent to the metallic film to form the sample.

2. The method of claim 1 which the rectangular area is approximately 3 mm by 180 µm.

3. The method of claim 1 which the base of the integrated TEM sample holder has a top surface approximately 100 µm from the first top surface.

4. The method of claim 1 in which the center portion is thinner than approximately 30 µm thick.

5. The method of claim 1 in which the removing steps include using a dicing saw.

6. The method of making an integrated TEM sample holder with a sample; comprising the steps of:

a. providing a semiconductor wafer having a top surface with a viewing site and a substantially parallel bottom surface;

b. forming a base of the sample holder suitable for engaging a TEM double-tilt holder including the steps of:

i. removing a slab of the wafer containing a top area containing the viewing site and a portion of the bottom surface suitably dimensioned for engaging a TEM double-tilt holder; and ii. removing a portion of the semiconductor material downwardly from the top surface of the slab to form a narrow center portion containing the view site; and c. thinning the center portion to form the sample.

7. The method of claim 6, further comprising depositing a metallic layer covering the viewing site.

8. The method of claim 7, in which the metallic layer includes platinum.

9. The method of claim 6, in which the removing steps include the using a dicing saw.

10. The method of claim 6, in which the base of the TEM sample holder is approximately 180 μm wide and 3 mm long.

11. The method of claim 6, in which the semiconductor wafer has a plurality of viewing sites.

12. The method of claim 11, in which a plurality of integrated TEM sample holders with a sample are formed from the semiconductor wafer.

13. The method of claim 12, in which the thinning the center portion of the plurality of sample holders is performed simultaneously in an ion-beam etching chamber.

14. The method of 6, further comprising the step of depositing an oxide film on the top surface of the semiconductor wafer, covering the viewing site.

* * * * *